Figure 1:
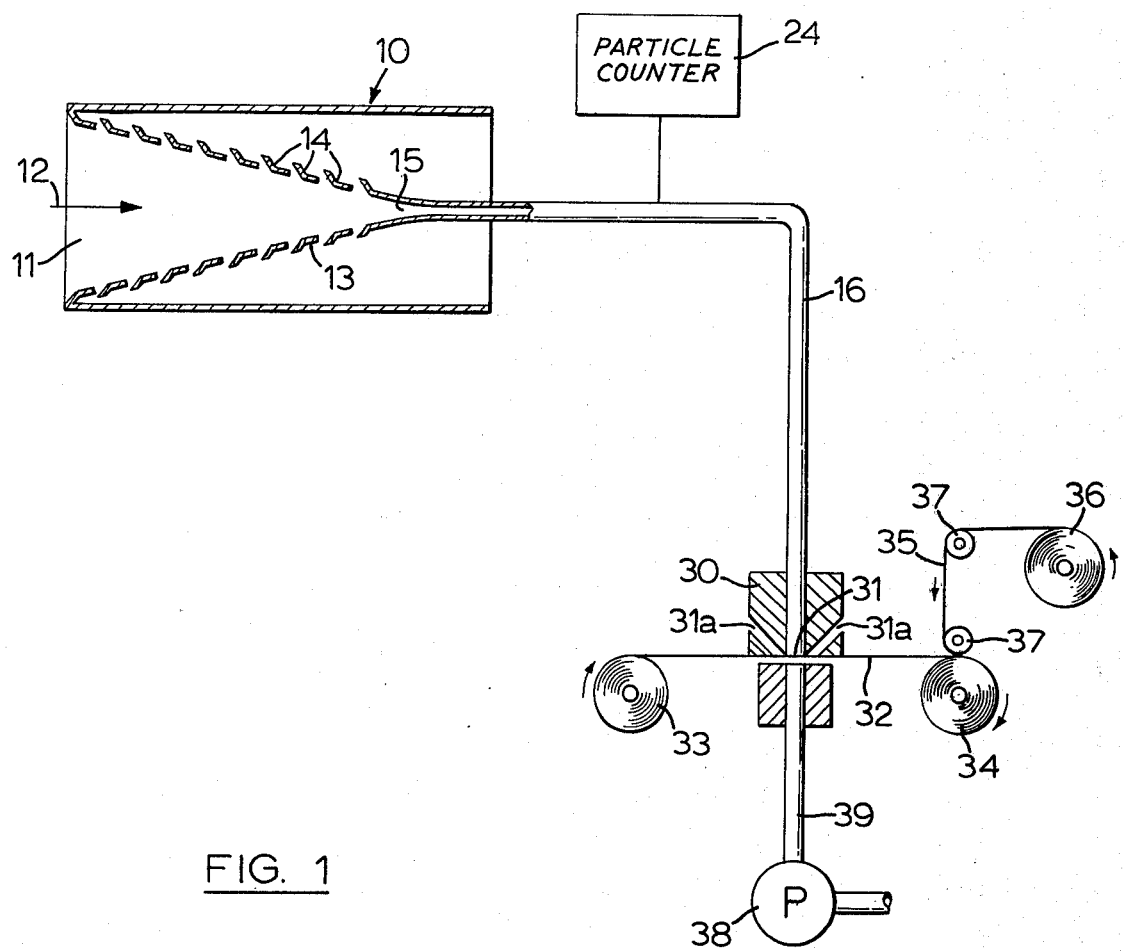

United States Patent [19]

Barringer

[11] 3,985,619

[45] Oct. 12, 1976

[54] EXPLORATION METHOD AND APPARATUS UTILIZING ATMOSPHERIC MICRO-ORGANIC PARTICULATES

[75] Inventor: Anthony Rene Barringer, Willowdale, Canada

[73] Assignee: Barringer Research Limited, Rexdale, Canada

[22] Filed: July 19, 1974

[21] Appl. No.: 490,153

[52] U.S. Cl. .................... 195/103.5 R; 195/103.5 P

[51] Int. Cl.² ........................ C12K 1/04; C12K 1/06

[58] Field of Search ............... 195/103.5 R, 103.5 P

[56] References Cited

UNITED STATES PATENTS

| | | | |
|---|---|---|---|
| 3,028,313 | 4/1962 | Oberdorfer et al. | 195/103.5 P |
| 3,033,761 | 5/1962 | Brown | 195/103.5 P |
| 3,127,329 | 3/1964 | Andersen | 195/103.5 R |
| 3,690,837 | 9/1972 | Witz et al. | 195/103.5 R |

FOREIGN PATENTS OR APPLICATIONS

| | | |
|---|---|---|
| 940,810 | 1/1974 | Canada |

*Primary Examiner*—A. Louis Monacell
*Assistant Examiner*—Esther L. Massung
*Attorney, Agent, or Firm*—Rogers, Bereskin & Parr

[57] ABSTRACT

Exploration method and apparatus in which atmospheric particulates are collected, and wherein micro-organisms present in the collected particulates are analyzed for pre-determined elements or compounds.

6 Claims, 1 Drawing Figure

EXPLORATION METHOD AND APPARATUS UTILIZING ATMOSPHERIC MICRO-ORGANIC PARTICULATES

This invention refers to a method and apparatus for detecting sub-surface mineral deposits, hydrocarbon accumulations and geothermal sources of energy, and in particular to the collection and analysis of atmospheric micro-organisms in exploration for mineral deposits, hydrocarbon accumulations and geothermal sources.

Micro-organisms such as bacteria tend to proliferate in specialized types on the surface of the earth according to the characteristics of nutrient materials available. Thus, in the presence of a mineral deposit containing copper sulphides, specific types of bacteria will multiply in the soils above the deposit such as sulphur bacteria and bacteria which are adapted to live in high concentrations of copper.

In the presence of a sub-surface oil field or gas field, there is a migration of methane, ethane and propane through fractures above the hydrocarbon deposit to the surface. In the surface regions of the soil, bacteria which utilize as a nutrient methane, ethane and propane will multiply. This effect even appears to occur in the oceans where subsurface seeps of gases into the ocean floor give rise to relatively high concentrations of these gases dissolved in the sea water and an accompanying growth of micro-organisms in the surface regions of the water which utilize these dissolved gases and nutrients.

A still further example of the phenomena occurs over buried geothermal sources in which the high temperatures of such regions tend to drive out volatile constituents of the rock such as mercury vapour and halogen vapours. Also, methane frequently occurs in geothermal regions. Such gases and vapours migrate upwards from great depths through overlying fracture systems to create strong localized growths of micro-organisms in the surface soils permeated by such seeps.

The present invention is based upon the discovery that micro-organisms living on the earths surface and which have a biochemical relationship with anomalous distributions of gases and elements attributable to mineral deposits, hydrocarbon accumulations and geothermal sources, not only exist on the earths surface but unexpectedly they also disperse continuously into the atmosphere in minute amounts. Further, it has been found that the distance of migration of living micro-organisms from their source areas on the earths surface surprisingly appears to be quite limited despite their small size, probably due to their limited ability to remain viable once suspended in the air. Many forms of bacteria and other microbes dehydrate within a period of minutes or less when levitated into the atmosphere due to the very high surface area of these microbes in relation to their body volume. In the case of mycobacteria, the dehydration can take place over hours or days due to the fact that the bacteria is covered by a thick pellicle of wax-like material. However, there are many forms of micro-organisms which are covered by only a very thin membrane which can be quite permeable and allow very rapid dehydration.

In the present invention, atmospheric particulates including micro-organisms are collected, for example from an aircraft or other vehicle traversing an area of the earth being explored, preferably concentrated, and then the collected micro-organisms are analyzed for content of pre-determined elements and compounds. The micro-organisms may be kept in a viable condition until the analysis is performed by depositing the particulates on a tape which may be covered with another tape, and preferably treated with a nutrient medium that will maintain the viability of the micro-organisms. For example, the tape may consist of a sterilized plastic that has been coated with agar. Micro-organisms such as bacteria can survive on such a tape for some time. In the laboratory, nutrients appropriate for specific micro-organisms or else a more general type of nutrient may be applied to the tape, and the micro-organisms on the tape may be incubated to cause colonies thereof to grow at positions of the tape wherein anomalous quantities of the micro-organisms were collected. After a suitable incubation period, the tape may quickly be inspected visually to determine those areas of the tape containing anomalous quantities of biological growth. Those areas of the tape are then carefully analyzed, for example by known spectrometric techniques, to determine the relative amounts of predetermined elements or compounds. This procedure cuts down considerably the amount of analysis required, because heretofore it was necessary to analyze virtually all of the tape.

As used herein, the term "micro-organism" refers to any small (e.g. below about 10 microns in size) living organism which is capable of reproduction, especially organisms such as bacteria which are nourished by deposits of economic importance and which are below about 5 microns in size.

Surveys may be performed according to the present invention from aircraft, or ground vehicles such as trucks or boats.

In the drawings:

FIG. 1 is a diagrammatic view of a preferred form of apparatus for carrying out the invention.

Referring to the drawings, a particle concentrator generally indicated by reference numeral 10 has an inlet 11 for receiving a moving stream of air containing particles. Arrow 12 indicates the direction of the air flow. The concentrator 10 may be installed in any convenient location on the aircraft or other vehicle, such as under a wing or in the nose, with the inlet 11 facing the direction of flight so that the greatest possible volume of air is received by the concentrator 11 per unit of time. Preferably the concentrator 11 should be dimensioned such that about ten cubic meters of air per minute passes through the inlet 11. In general, the greater the rate of flow of incoming air, the better. Of course, the size of the aircraft or other vehicle may dictate a practical upper limit. Also, two collectors may be employed if capacity of the aircraft permits. Although it is advantageous to concentrate the particulates in this manner, it is not considered essential to do so because even a single bacteria, for example, can be caused to multiply to the extent that analysis is facilitated.

Air which has passed through the inlet 11 of the concentrator 10 strikes walls 13 of the concentrator 10 at high velocity and particles bounce off the walls 13 towards the apex of the concentrator 10. The walls 13 may be arranged to form a pyramidal or conical shape, and the walls 13 are formed of sheet metal that has been cut and worked to form a plurality of small louvres 14 which are disposed at an acute angle to the direction of the incoming air. This arrangement allows air to escape through the louvres 14, but most of the particles do not escape since they have considerable inertia and are unable to turn through the sharp angles required to escape through the louvres 14. Very fine particles (e.g. below about one micron in diameter) are entrained in the air and tend to escape through the louvres 14 with the air. It is desirable to dimension the louvres 14 such that the turning radius required for a particle to escape through a louvre opening is minimal, so that statistically the majority of particles will strike the walls 13 of the concentrator 10 and not escape through the openings of the louvres 14. It has been found that openings of a length of about 2 cm., width of 4 mm, provide satisfactory results. Preferably the angle between the louvres 14 and the wall 13 is about 30°. Alternatively, a cyclone of the kind shown in copending Canadian patent application No. 932,252 of Barringer Research Limited could be used.

A concentrated stream of particles emerges from apical outlet 15 of the concentrator 10 and is fed into a tube 16. It is desirable to monitor the mass flow rate of the stream of concentrated particles to provide a measure of normalization. This may be accomplished, at least approximately, by means of a conventional light scattering particle monitor 24 that is normally used for measuring particulate concentrations on a dynamic basis. Essentially, the monitor 24 provides a beam of light (e.g. from a laser source) which illuminates the particles and measures the light scattered by the particles. The monitor 24 may be installed immediately downstream of the concentrator 10. Alternatively, or in addition to the above, the system may be normalized against a common element or compound not related to mineralization such as silicates in the case of a land system and chlorine in the case of an off-shore system. In such cases the silicate or chlorine content of the particles would separately be measured, and the measurement of the predetermined elements or compounds of interest would be compared with the measurement of the said common element. Normalization is not extremely critical, however, as useful results have been attained without any normalization.

The stream of concentrated particles travels along the tube 16 to a nozzle 30 having an orifice 31 through which the concentrated particles emerge. The nozzle 30 is also formed with diagonally extending air vents 31a which bleed off a substantial amount of the air contained in the stream of moving particles.

After emerging from the nozzle 30, particles are directed against and captured by a continuous length of porous polytetrafluorethylene tape 32 which is wound around a feed reel 33 and a takeup reel 34. The tape 32 is constructed of sterilized thin, strong, non-contaminating porous plastic tape that allows suction of air through the tape and filtration of particles onto the surface of the tape. A suitable tape made from polytetrafluoroethylene which has been treated to provide it with large numbers of small holes having diameters of less than 3 microns is manufactured by W. L. Gore Associates Incorporated and is identified by No. L10068 or L10069. Air is sucked through the tape 32 by a vacuum pump 38 through a tube 39 which is connected to an apertured support plate 40.

In order to protect the particles from contamination by the atmosphere and to provide a nutrient to keep the micro-organisms alive, a nutrient impregnated cover tape 35 is wound around a feed reel 36 which is guided by several guide rollers 37 so that the tape 35 runs parallel to the tape 32 downstream from the nozzle 31, and after being pressed together the tapes 32 and 35 are wound together on the takeup reel 34. The tape 35 may be fabricated from filter paper tape such as Whatman type 541 SFC manufactured by W. & R. Balston Ltd. The tape 35 may also be impregnated with a nutrient agar solution. The agar is allowed to set on the tape and thereafter the tape is kept hermetically sealed to prevent drying or contamination of the agar. The entire tape mechanism should be enclosed in an air tight container to exclude contaminating materials and to prevent dehydration of the nutrient tape.

A conventional marking and numbering device (not shown) is used for providing numbered fiducial marks at regular periodic intervals on the tape 32. In the result, a continuous strip of particulate material is deposited on the tape, or a series of spots if the tape is advanced step-wise. In either mode of operation of the tape 32 it is desirable to achieve a resolution of the tape 32 equivalent to not more than 1,000 feet on the ground. Thus, in an aircraft flying at about 100 m.p.h. it is desirable to achieve a time resolution of 10 seconds or less.

When employed in airborne survey the apparatus may be used in conjunction with an airborne flightpath camera which provides continuous 35 mm. photography of the ground. A typical survey may be performed at an altitude of 200 feet in parallel traverses which typically are 1/5th of a mile apart. Thus, a grid pattern is laid down over the area to be surveyed and samples are collected on the tape 32 representing increments of not more than 1,000 feet along the flight lines. Numbering and fiducial markings on the tape 32 can be related to similar numbering of fiducial marks on the flightpath camera. This enables a precise correlation to be obtained between the tape 32 and the location of the aircraft over the ground. When the equipment is mounted in an aircraft carrying out surveys over the ocean, it is necessary to employ electronic navigation aids to provide guidance to the survey aircraft and fix its location. In carrying out processing of the tape 32, additional nutrient can be supplied in the form of a solution applied to the tape 32 and absorbed in the agar. The tape 32 may then be placed in an incubation chamber at an appropriate temperature. As an alternative an active nutrient can be employed in the initial coating on the tape 32 and the particles may be deposited on the tape 32 in the environment of a gas selected to retard incubation during the survey, or alternatively the tape 32 can be held at a low temperature that will inhibit multiplication of micro-organisms. It is convenient to arrange for incubation and multiplication of the micro-organisms to be carried out following the completion of survey flights under precisely controlled conditions. Conventional micro-biological techniques may be employed in this regard. At appropriate temperatures in the presence of appropriate nutrients strong growths of micro-organisms will be found to occur over localized areas of the tape 32. It has been found that such growths occur over regions containing large amounts of sulphur, or places where hydrocarbon gases are seeping out of the ground. These regions tend to be ones of considerable interest from the point of view of natural resources.

A more advanced method of handling the tape 32 is to immerse the tape 32 in a radioactive medium. For example, if it is desired to prospect for copper deposits, the tape 32 can be treated with a copper sulphate solution in which a radioactive isotope of copper is employed. It has been found that specialized forms of bacteria proliferate over copper deposits and that these bacteria are not only able to withstand high concentrations of copper, but become dependent upon copper as a nutrient. Thus, in the presence of a copper sulphate solution the only bacteria that will multiply will be bacteria of this type, and they will take up radioactive copper actively into their cells. If the tape is incubated for an appropriate period of time, such as one week in the presence of this nutrient, it can subsequently be washed to remove radioactive copper in solution and then subjected to radiation counting with a nuclear counter in order to measure radiation from radioactive copper. It has been found that strong patches of radioactive copper will accumulate on the sampling tape at points which represent atmospheric samples taken over sub-surface copper deposits.

This radioactive technique can be applied to the identification of a large range of specialized types of bacteria. The method has the special advantage that simultaneous detection of various types of bacteria can be carried out. Thus, a solution containing both radioactive zinc and radioactive copper can be used in simultaneously looking for specialized zinc and copper consuming bacteria. The use of suitable counting equipment in the nuclear readout system can differentiate between radioactive zinc and copper allowing the localized sources of each to be identified. The technique can be extended to other metals and also to gases such as methane and ethane. In the latter case, methane containing radioactive carbon can be employed and similarly for ethane. The uptake of these gases into the micro-organisms is measured by monitoring radiation from the tape 32.

A somewhat less sophisticated approach is to apply individual nutrients specific for certain types of bacteria and to identify the number of colonies growing and their locations on the tape. This is a satisfactory technique when looking solely for one type of micro-organism such as ethane consuming bacteria.

In order to achieve high resolution, it is possible to deliberately culture only those bacteria which do not form spores and which have short life times in the atmosphere. These can migrate only very short distances and have a tendency to be very highly localized indeed.

An alternative system for defining the localized source of bacteria is to measure the moisture content of the incoming particulate stream. It has been found that the moisture content of particulates can increase considerably over the source of active dispersion of micro-organisms. A typical water content of a bacteria is in excess of 90% prior to dehydration, however, the water content of this bacteria will reduce to the order of 20% or less if it dehydrates in the atmosphere or if it turns into a spore. Various methods can be used for monitoring the water content of the particulate stream. For example, the stream may be split into two, one half being supplied to the sampling tape and the other half to a coiled heating tube which pyrolyzes the particulates and drives off the water vapour. This water vapour may be measured by any one of a large number of methods including infrared transmission, development of dew on a chilled surface subject to photoelectric monitoring, spectrographic emission, etc. Monitoring water content, therefore, can provide a very simple means of pinpointing strong and active microbiological emissions.

What I claim is:

1. A method of prospecting for mineral deposits, hydrocarbon accumulations and geothermal sources comprising:

a. traversing an area of the earth, b. collecting particulate matter contained in the atmosphere above the earth, said particulate matter containing micro-organisms and said particulate matter being collected at a plurality of different positions in said area, c. determining the geographical location of each different position in which said particulate matter was collected, d. concentrating said particulate matter immediately after it has been collected, e. storing said particulate matter in a medium that is adapted to maintain the viability of the micro-organisms contained therein, f. applying a nutrient to said particulate matter and incubating at least a portion of said micro-organisms, whereby said micro-organisms are caused to multiply, and g. observing the locations on said medium at which anomolous growths of said micro-organisms have occurred, and correlating said locations on said medium with said geographical locations.

2. A method as claimed in claim 1 wherein after the particulate matter has been collected, a radioactive substance is applied to said particulate matter which is capable of being absorbed in the cells of said micro-organisms, wherein non-absorbed quantities of said radioactive substance are subsequently removed, and wherein said micro-organisms are analyzed by measuring radioactive emissions from said particulate matter.

3. A method as claimed in claim 1 wherein the step of applying said nutrient includes culturing only non-spore forming bacteria of said micro-organisms.

4. A method as claimed in claim 1 wherein the micro-organisms are analyzed by measuring the water content of said particulates.

5. A method as claimed in claim 1 wherein after the said micro-organisms are caused to multiply, the collected particulate matter is analyzed for predetermined elements or compounds present in said micro-organisms.

6. A method as claimed in claim 1 wherein said storing step comprises applying said particulate matter to a movable non-contaminating strip, said strip being moved at a predetermined rate.

* * * * *